United States Patent [19]

Newman

[11] Patent Number: 5,271,893
[45] Date of Patent: Dec. 21, 1993

[54] APPARATUS FOR STEAM STERILIZATION OF ARTICLES

[76] Inventor: Duncan Newman, 314 Kenilworth Avenue, Toronto, Ontario, Canada, M4L 3S8

[21] Appl. No.: 762,797

[22] Filed: Sep. 20, 1991

Related U.S. Application Data

[63] Continuation of Ser. No. 440,689, Nov. 24, 1989, abandoned.

[51] Int. Cl.$^5$ .............................................. A61L 2/06
[52] U.S. Cl. ...................................... 422/26; 422/11; 422/3; 422/112; 422/116
[58] Field of Search ......... 422/11, 26, 33, 3, 111–112, 422/298, 299, 6; 122/451.1, 479 R, 479 S, 487

[56] References Cited

U.S. PATENT DOCUMENTS

| | | |
|---|---|---|
| 1,960,890 | 5/1934 | Bidwell . |
| 3,107,975 | 10/1963 | Linder . |
| 3,481,692 | 12/1969 | Linder . |
| 3,717,434 | 2/1973 | Black . |
| 3,773,466 | 10/1973 | Linder . |
| 4,309,381 | 1/1982 | Chamberlain et al. . |
| 4,541,992 | 9/1985 | Jerge et al. . |
| 4,748,003 | 5/1988 | Riley . |
| 4,778,113 | 10/1988 | Jewett et al. . |
| 4,854,475 | 8/1989 | Riihimaki et al. . |

FOREIGN PATENT DOCUMENTS

WO85102108 5/1985 PCT Int'l Appl. .

OTHER PUBLICATIONS

Advertising brochure of E. A. Beck & Co. of Costa Mesa, Calif. for Brevet Cassette Sterilization Module.

Primary Examiner—James C. Housel
Assistant Examiner—Lyle Alexander
Attorney, Agent, or Firm—Dickinson, Wright, Moon, Van Dusen & Freeman

[57] ABSTRACT

A process, system and pressure chamber for the automated sterilization of articles, particularly medical or dental instruments is disclosed, which is simple to use and economically efficient by comparison with conventional autoclaves and steam sterilizing system. Steam is generated by the pulsed injection of a controlled quantity of water into a heated boiler whenever it runs dry. The boiler is coupled in a closed-loop system to a relatively small pressure chamber in the form of a cassette that is readily inserted and removed from a holder connecting the chamber to a steam inlet conduit and a venting conduit, the latter being closed off during pressurization of the chamber. By automated monitoring of the boiler and chamber temperatures, conditions in the chamber are measured and the boiler and valves in the system controlled to effect a sterilization cycle.

10 Claims, 11 Drawing Sheets

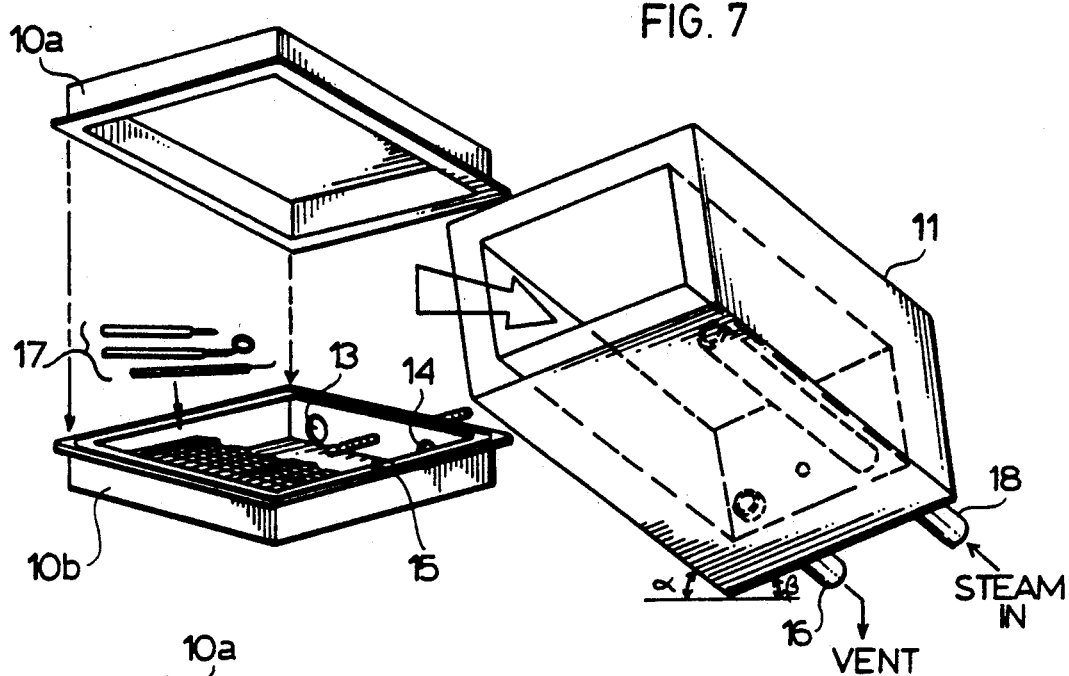
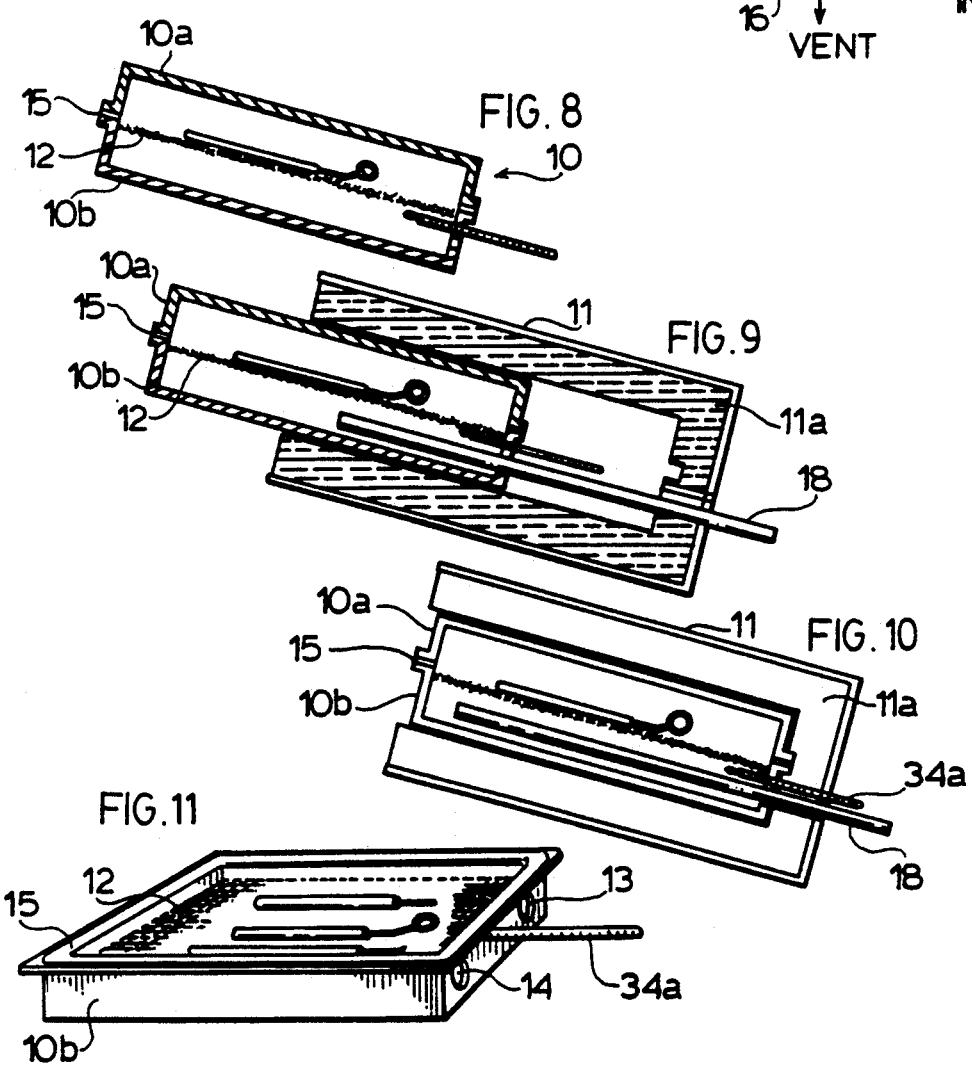

APPARATUS FOR STEAM STERILIZATION OF ARTICLES

This is a continuation of U.S. application Ser. No. 07/440,689 which was filed on Nov. 24, 1989, and is abandoned.

TECHNICAL FIELD

This invention relates to a process and apparatus for the steam sterilization of articles. More particularly, this invention relates to a system for the efficient sterilization of dental or surgical instruments or the like.

BACKGROUND

Flow-through sterilizers of the type used in hospitals or in industrial applications are generally provided with access to a source of saturated steam "on tap" which is used to purge air from a chamber containing the articles to be sterilized and to heat the load until sterilization exposure is complete.

In the usual dental or medical office, it would be physically and economically impractical to have an available steam line, and so sterilization of instruments in these applications has hitherto been carried out using standard autoclaves. An autoclave is typically a relatively large sealed vessel which contains a quantity of boiling water under pressure. Such an instrument is generally provided with a lower exit vent which is initially kept open for a period while water is boiled inside the autoclave to purge the air from the interior. As air is incompatible with and denser than saturated steam, it tends to be pushed out the exit valve ahead of the steam.

Nevertheless, the standard arrangement can lead to appreciable quantities of air being retained in the autoclave chamber, necessitating the simultaneous measurement of both pressure and temperature conditions in the chamber if one is to have confidence in the sterilizing conditions to which the contents are exposed. Imperfect purging of air or an incorrect interpretation of the simultaneous readings of the mutually dependant variables of temperature and pressure could present a biological hazard. On the other hand, unduly high temperatures in the standard autoclave can, with time, damage the contents.

Moreover, in a closed system such as the standard autoclave, or in other known systems which employ a circulating water phase, contaminants from the instruments constantly build up with time, leading to corrosion of the autoclave walls, and possible damage to the contents. A further practical disadvantage of standard autoclaves is their inherent slowness, due to the large heat capacity of their heavy walls and support structures.

SUMMARY OF THE INVENTION

It has now been found that the aforementioned disadvantages of standard autoclaves can be overcome by the novel sterilizing system of the invention, which is of a simple construction, adapted to be contained within a relatively small and lightweight benchtop unit. Economy and efficiency of the sterilization process, as well as increased speed of operation over the standard autoclave is achieved by mating a relatively small pressure chamber, preferably in the form of a thin-walled and insulated flat tray, to a controlled electrical boiler which generates steam as needed to produce a sterilizing condition inside the chamber.

In one aspect, the invention is a process for the steam sterilization of articles by the controlled delivery of steam from an electrically heated boiler in communication with a pressure chamber through a steam delivery conduit. The process comprises generating steam by the pulsed injection of a controlled quantity of water into the heated boiler whenever it runs dry. The steam from the boiler is permitted to pass into the chamber while a venting conduit from the chamber is open, to expel the air initially therein. The venting conduit is then closed, so that steam generated in the boiler raises the pressure and the temperature in the chamber. The temperature in the chamber is monitored until the desired sterilization temperature is attained, then the temperature in the chamber is controlled to remain substantially constant at the sterilization temperature for a desired period. This control is achieved by modulating the electric power supply to the boiler heater. At predetermined intervals during pressurization of the chamber and during maintenance of the sterilization temperature within the chamber, the venting conduit from the chamber is opened to cause condensed liquid water from the chamber to be purged therethrough. The venting conduit is then closed and, upon completion of sterilization, the boiler is turned off and the venting conduit opened to exhaust the chamber and return it to atmospheric pressure.

In another aspect, the invention is a system for steam sterilizing articles, comprising a pressure chamber for holding the articles to be sterilized, having an inlet conduit for steam and an outlet conduit; valve means for venting the interior of the chamber; and means for injecting steam into the chamber comprising a controlled electric boiler in communication with the pressure chamber through the steam inlet conduit and a pump operable to inject pulses of water into the boiler to produce steam. The system includes sensor means for monitoring the temperature of steam in the chamber and for detecting dryness of the boiler. The aforementioned process of the invention is carried out by the system of the invention under the control of sequencing means responsive to the various sensor means.

In a final aspect, the invention is a sterilization chamber and associated holder, the sterilization chamber comprising a tray to receive instruments to be sterilized and a lid with a pressure seal between the two. The holder, into which the assembled tray and lid may be slid as a cassette, couples the chamber to an external supply of steam and to a venting conduit, and maintains the tray and lid in pressure tight relationship. In a preferred embodiment, the cassette pressure chamber comprises a shallow bottom tray and a shallow rectangular lid which together form the chamber when the lid is placed over the tray. Perimetrical self-actuating sealing means between the tray and the lid are so configured to define a channel which is closed between the wall of the tray and the wall of the lid in the region of a first end of the chamber, but which partly opens into the interior of the pressure chamber at an opposite end of the chamber. A steam inlet duct at the first end of the chamber communicates with the interior of the channel and feeds steam along the channel towards the opposite end of the chamber where the steam is distributed through the opening portion of the channel, passes over the instruments sterilizing them and is then vented through an outlet duct in communication with the interior of the chamber positioned nearby the inlet duct.

Other objects and advantages of the invention will be evident from the following description referring to the accompanying drawings illustrating the process of the invention, a sterilization system according to the invention, and a pressure chamber according to the invention, in which corresponding components are identified with the same reference numerals.

BRIEF DESCRIPTION OF THE DRAWINGS

FIG. 7 is an exploded schematic view of a cassette sterilization chamber and holder according to the invention;

FIG. 8 is a sectional view from one side of the assembled cassette sterilization chamber of FIG. 7;

FIG. 9 is a sectional view from one side of the cassette sterilization chamber of FIG. 8, shown partially inserted into the associated holder;

FIG. 10 is a sectional view from one side of the cassette sterilization chamber of FIG. 8, shown fully inserted into the associated holder;

FIG. 11 is a perspective view of the bottom tray of the cassette sterilization chamber holding sterilized instruments following completion of a sterilization process;

DETAILED DESCRIPTION OF THE PREFERRED EMBODIMENT

Efficiency, rapidity and economy in the sterilization of dental and surgical instruments and the like is achieved according to the apparatus and process of the invention by providing a one-way flow system in which a sterilization chamber is fed with steam as required from a boiler operating as a "flash" boiler.

Figure 1:
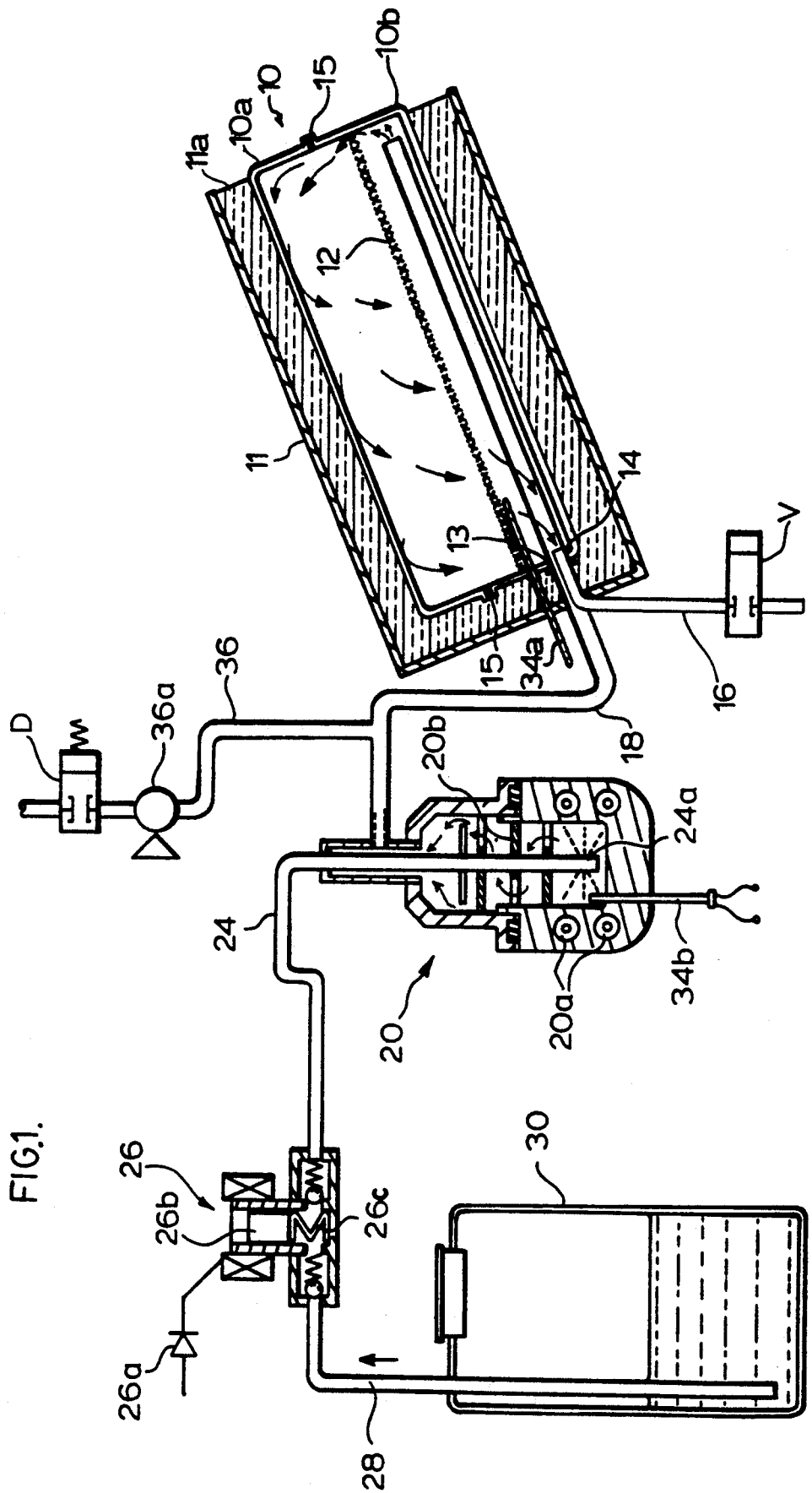
FIG. 1 illustrates schematically and in cross-section the arrangement of components in a sterilizing system according to the invention, excluding the sequencing means and conventional interfacial relays controlling operation of the system.

FIG. 1 illustrates semi-schematically in vertical cross-section a preferred embodiment of a system according to the invention for the steam injection sterilization of articles in a pressure chamber 10.

It is emphasized that the utility of the steam sterilization process of the invention and of the system of the invention are not restricted to one particular form of pressure chamber or autoclave for holding the articles to be sterilized. According to one aspect of the invention, however, described in further detail below in connection with FIG. 7 to 11 there is provided and shown in use in the system of FIG. 1, a novel sterilization chamber in the form of a "cassette" that can be inserted into a rigid holder 11 with an insulating lining 11a, designed to couple the inserted chamber to a steam inlet 18 and a vent conduit 16 The cassette comprises a tray 10b to receive the instruments and a lid 10a with compressible pressure sealing means 15 between the two. The lid 10a can be simply lifted off the tray 10b for loading and unloading, but the holder 11 is designed to maintain the lid and tray in sealing relationship when the cassette is placed in the holder.

Because the system of the invention operates by first purging air from the chamber then sealing the chamber and injecting steam in a controlled manner to bring the chamber interior up to a sterilization temperature, steam should enter the chamber at an end remote from the outlet from the chamber to assist in the initial purging of air therefrom The outlet port, indicated at 14 in FIG. 1, should be disposed at the lowest point in the chamber 10 to permit purging of the liquid water that forms when sterilizing steam condenses in heating the articles in chamber 10, which are preferably laid out prior to sterilization on a perforated grid or rack 12 inside the chamber In the case of a cassette pressure chamber 10 as illustrated in FIG. 1, this can simply be achieved by having the chamber mounted in use at an angle such that condensate runs under gravity toward the outlet, but it will be appreciated that any of a number of simple arrangements and construction of pressure chamber will achieve this, any of which must, of course, provide for access of instruments into the chamber prior to commencement of steam injection, and means for sealing the chamber during use.

In the illustration of FIG. 1, chamber 10 is provided at the bottom thereof with an inlet port 13 and an outlet port 14. The outlet port sealingly receives an outlet conduit 16 including a first valve V (for "venting") which may be switched between an open position in which steam, air or condensed water may pass from inside chamber 10 through conduit 16 and into a waste water container. Steam injection conduit 18 is sealingly received in inlet port 13.

The sequence of steps carried out in a sterilization process according to the invention requires the ability to monitor the temperature inside the chamber 10 when it is being pressurized by steam or is being held at the desired steam sterilization condition. As seen in FIG. 1, a thermocouple or thermistor 34a extends into chamber 10 in the vicinity of outlet port 14 when the cassette chamber is connected to its inlet and outlet conduits. The signal from thermocouple sensor 34a provides the requisite measure of temperature.

As seen in FIG. 1, boiler 20 includes a water injection conduit 24 leading from a dosing pump 26, which may be actuated to draw distilled water through feed line 28 from a container 30 of distilled water and inject a pulse of water of a preset size into boiler 20. As a dosing pump, there may be employed any low-volume high-pressure pump operable to inject a pulse of water when actuated. A preferred component for this purpose is a solenoid plunger pump, whose power input includes a rectifying diode 26a to provide unidirectional pulsing of the pump plunger 26b against a biasing spring 26c.

Boiler 20 is heated by electrical heating elements 20a supplied with electrical power from a switchable power source (not shown). In a typical installation for use in the sterilizing of dental or surgical instruments, boiler 20 will have an interior capacity of around 50 ml., with heating elements 20a providing around 1 kW of power.

It is important that the boiler capacity be sufficiently small relative to the volume of water pulsed into it by each injection from dosing pump 26 to ensure early and complete purging of air from the boiler interior. This is achieved if the volume of water dosed into the boiler is not much less than about 20 percent of the boiler volume. Ideally, the interior volume of the boiler should be no greater than necessary to permit free boiling of the water pulses pumped into it.

Inside the boiler for rapid conversion to steam. Distilled or demineralized water should be used to avoid the build-up of mineral deposits around the below-described dryness sensing means in the boiler. The interior space of the boiler may advantageously be provided with a plurality of stainless steel baffles 20b, to prevent splashover of boiling water into steam injection conduit 18 and to minimize the formation of aerosol droplets of water, which would not transfer heat of vaporization to articles in pressure chamber 10. "High quality" steam having a low aerosol content is thereby fed into the steam injection conduit 18.

The opening and closing of valve V may be controlled by using as valve V a solenoid two-way valve with conventional electrical switching means (not shown). Pump 26 may likewise be actuated to inject a pulse of water by means of a conventional solenoid and switch arrangement.

In addition to monitoring the temperature inside the chamber 10, it is necessary for the process of the invention to be able to detect when boiler 20 has run dry, so that a fresh pulse of water may be injected using dosing pump 26. The means for detecting dryness of the boiler in the embodiment illustrated in FIG. 1 comprises a second temperature sensor 34b such as a thermocouple or thermistor, fixed within the casing of the boiler at a position intermediate heating elements 20a and the interior cavity of boiler 20. Evaporation of water in the boiler to dryness is then detected by an abrupt increase in the sensed temperature as a function of time.

For that embodiment of the process further including a "deviation check" as described below, it is also advantageous for sensor 34b to project a small distance into the interior cavity of boiler 20, so that sensor 34b is in contact with the casing metal, but also exposed to the steam generated within the boiler, as indicated in FIG. 1. By this arrangement, the sensor is operable not only to detect abrupt heating of the casing when the boiler runs dry, but also to provide a measure of the equilibrium steam temperature (boiling point) inside the boiler which may be compared with the steam temperature in the chamber 10.

Figure 2:
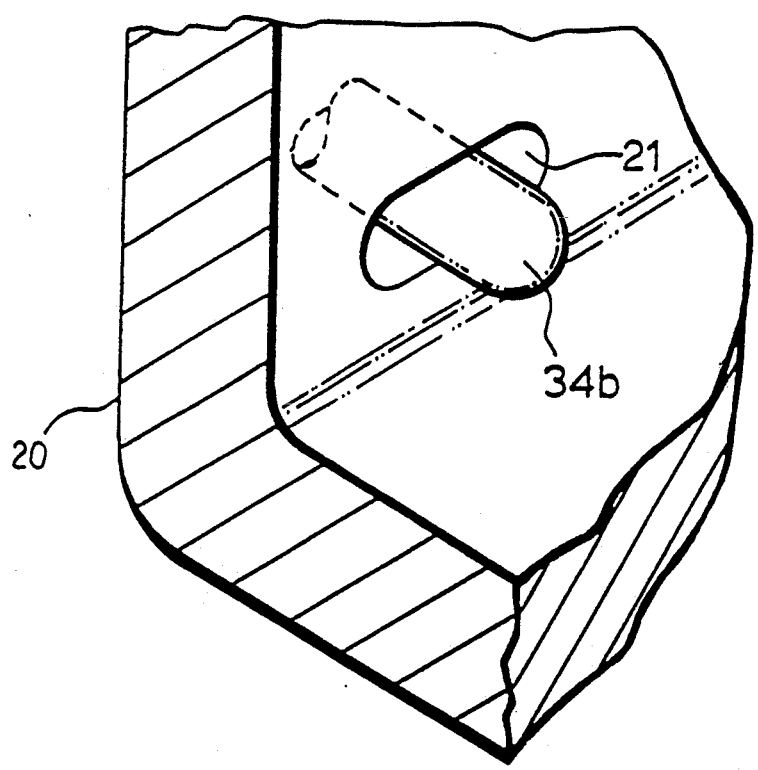
FIG. 2 is a detailed view of the location inside the boiler of FIG. 1 where the tip of a temperature sensor enters.

One arrangement for permitting thermocouple 34b to contact the boiler casing while exposed to steam therein is illustrated in FIG. 2. The tip of the sensor is surrounded by a shallow out-of-round recess 21 formed in the casing wall, so that it contacts the top and bottom inner surfaces of recess 21, which at the same time permits the access of steam around much of the sensor tip's surface.

Figure 3:
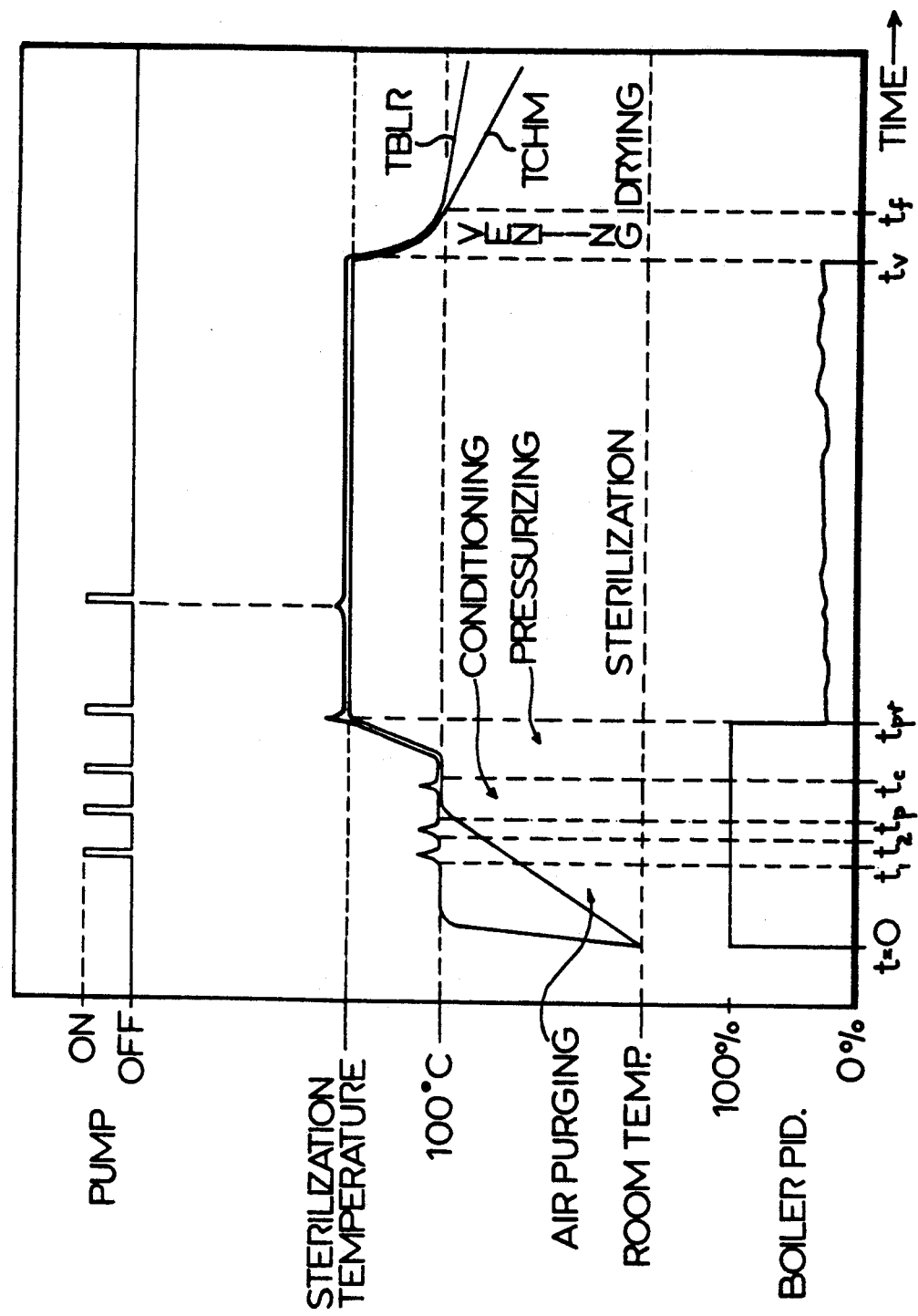
FIG. 3 is an idealized graphical representation of various operational parameters in the process of the invention as a function of time over the course of a sterilization cycle.

FIG. 3 presents four idealized graphical representations of the concurrent variation with time of parameters of operation. From top to bottom, these are: (1) the pulsed injection of water into the boiler, (2) the temperature reading, TBLR from a boiler temperature sensor 34b installed as in FIG. 22, (3) the temperature reading TCHM from the chamber thermocouple 34a, and (4) the control of power delivered to the boiler heating elements 20a.

After a time $t_1$ has elapsed following injection of a pulse of water into the boiler, evaporation of the water to dryness is signalled by a sharp increase in the slope of the boiler temperature TBLR. Injection of a short-duration pulse of water at that time drops the value of TBLR until some later time $t_2$ when the injected pulse has evaporated and the dryness signal calls on pump 26 to inject a further pulse of distilled water, and so on whenever dryness of the boiler is detected.

The process of steam sterilization of articles according to the invention will now be described in connection with the embodiment of the system of the invention illustrated in FIG. 1 and the time graphs of FIG. 3:

At the outset of the sterilization cycle, indicated as $t=0$ on the graphs of FIG. 3, the boiler power is turned on and a pulse of water is injected, generating steam. A flow of steam is generated in boiler 20 by the pulsed injection by pump 26 of a controlled quantity of water into the hot boiler, whenever dryness of the boiler is detected.

In the initial purging phase, from $t=0$ to $t=t_p$, the steam generated in boiler 20 passes through steam injection conduit 18 into chamber 10 to expel the air initially therein through outlet conduit 16, by way of opened valve V. The importance of effective air removal in steam sterilization processes is well known. A novel pressure chamber according to the invention, which is particularly efficient in this respect, is described in detail below in connection with FIGS. 7 to 18.

In the purging phase of the sterilization cycle, the air initially present in the chamber is expelled and TCHM rises from room temperature to around 100° C., the equilibrium temperature of saturated steam at atmospheric pressure.

As steam is allowed to pass through the chamber during the purging phase, the temperature of the effluent stream vented from the pressure chamber is monitored using sensor 34a. Once that temperature has risen to about 100° C., indicating substantial purging of air from the chamber, steam is allowed to pass through for a selected conditioning period, from $t=t_p$ to $t=t_c$ in FIG. 3, to ensure the elimination of air from the system, and then valve V is closed, so that steam generated in boiler 20 commences to pressurize the chamber. During the pressurization phase, from $t=t_c$ to $t=t_{pr}$ in FIG. 3, as in the previous purging phase, boiler 20 remains turned on at its full power and steam continues to be generated from the pulses of water injected into the boiler by pump 26.

During this pressurization phase of the cycle, the interior of the boiler and the pressure chamber form a closed system and go up in temperature together as the equilibrium temperature for saturated steam rises with increasing pressure. Over this period, the difference TBLR - TCHM is a more sensitive measure of the onset of dryness in the chamber than is TBLR alone.

The temperature of the chamber is monitored until a desired sterilization temperature is attained. The selected temperature of sterilization may be as low as about 124° C., when the articles being sterilized are instruments including rubber or thermoplastic components susceptible to damage at higher temperatures. When the articles are simple stainless steel dental instruments, a sterilization temperature of up to around 145° C. may be used for correspondingly reduced sterilization exposure times. The point of attainment of the selected sterilization temperature is shown to have occurred at time $t = t_{pr}$ in FIG. 3. From that point until the completion of sterilization exposure of articles in the chamber (at time $t = t_v$) in the chamber is controlled to remain substantially constant at the sterilization temperature.

This sterilization temperature control may be effected by switching the electric power supplied to the boiler cyclically off and on. Computer sequencing means controlling the operation of the system may readily be programmed to monitor a moving average of TBLR and to adjust the duty cycle of power delivered to the boiler heaters as necessary to minimize variations in TCHM. This is referred to in FIG. 3 as the PID (proportional integral derivative) control of the boiler duty cycle.

Throughout the pressurization and sterilization phases, pump 26 continues to deliver controlled quantities of water in response to sensed dryness of the boiler. The amount of steam produced increases with the mass to be heated to equilibrium with the saturated steam. Production of steam "on demand" in this manner is far less wasteful of both water and energy than known sterilizing systems. For a 2 litre capacity sterilization chamber constructed as described below, used in the above-described sterilization system employing a 50 ml. boiler, only about 70 mls of distilled water is used up in sterilizing a typical tray of surgical or dental instruments.

Upon completion of the desired sterilization period at time $t = t_v$ vent valve V is opened to exhaust the chamber and return it to atmospheric pressure, and the boiler is turned off. Following venting of the chamber and its return to atmospheric pressure ($t = t_v$), the sterilized instruments may be cooled to a usable temperature simply by removing and opening chamber 10. Alternatively, the system in the embodiment of FIG. 1 is provided with a source of clean, dry compressed air connected to an air conduit 36 and regulator 36a branching from steam injection conduit 18. At the conclusion of the sterilization cycle, compressed air may be admitted to line 36 and thence into the chamber via conduit 22, by actuating valve D in the compressed air line. Compressed air (which may first be pre-warmed and/or passed through suitable microbial filters) is then passed over the instruments to hasten cooling and drying (time $t \geq t_f$ in FIG. 3).

Alternative arrangements for cooling down the articles in the chamber at the conclusion of sterilization will be readily apparent to those of ordinary skill in the art.

Thus, for example, if chamber 10 were provided with check valve means or with self-actuating sealing means operable to admit a flow of atmospheric air into the chamber only when the pressure inside the chamber is below ambient pressure, then a vacuum system could be used to draw out excess condensate from the outlet conduit and draw cooling air into the chamber. The vacuum could be produced by an appropriate vacuum pump. Alternatively, boiler dosing pump 26 of FIG. 1 could itself be shunted to power a jet pump (eductor) to draw a vacuum by aspiration. Such an eductor pump might alternatively be powered by a jet of steam from boiler 20.

Figure 4:
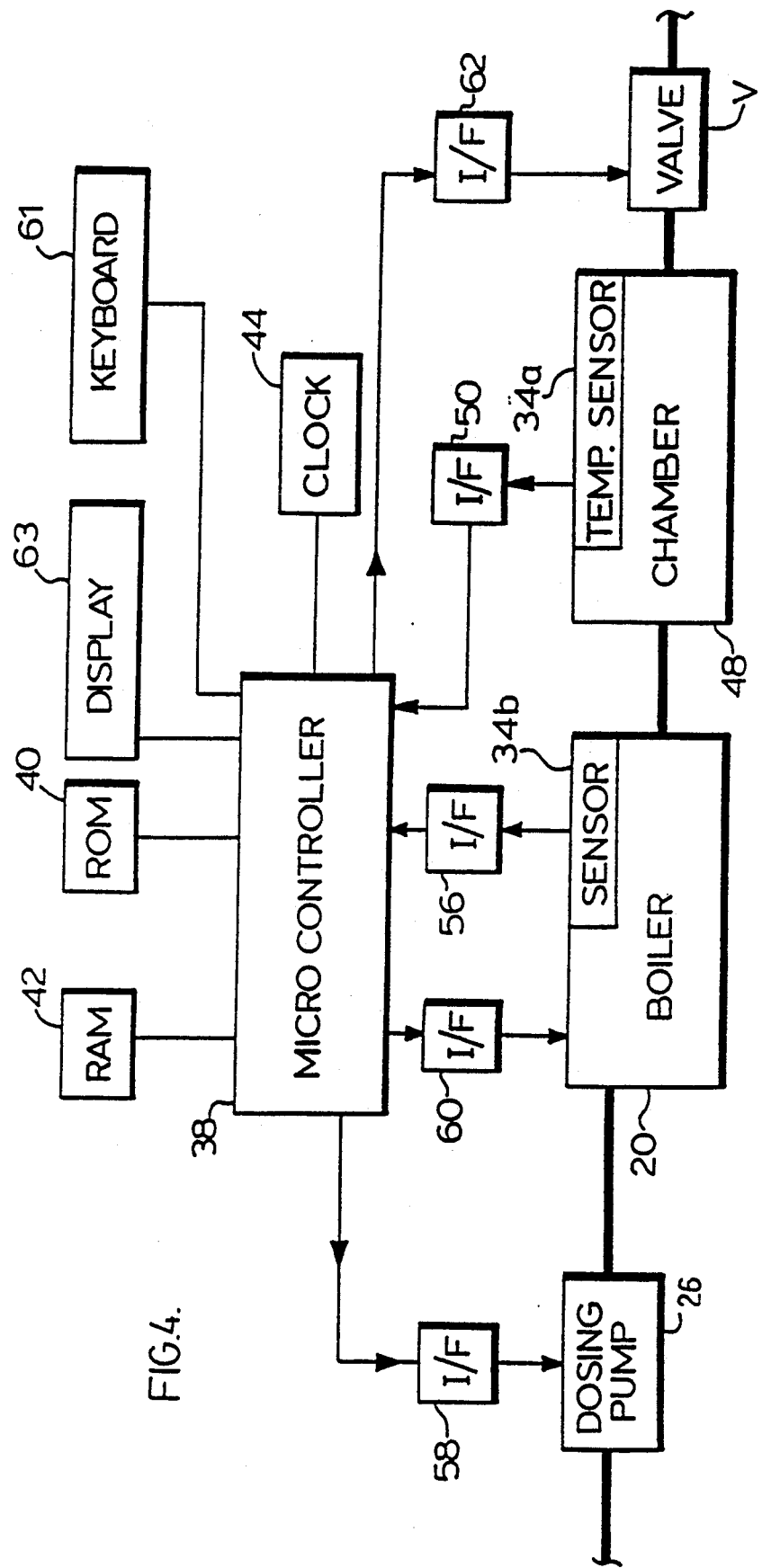
FIG. 4 is a schematic representation of the system of the invention, including microprocessor sequencing (controlling) means and the connections to operating components of the system, in which a heavy line connection represents a flow of water, steam or air and the light lines represent electrical connections.

FIG. 4 illustrates electronic processor apparatus for controlling the operation of the system of FIG. 1 according to the process of the invention.

Microcontroller 38 includes a program memory 40, working memory 42 and a timer clock 44. The microcontroller is responsive to the temperature sensor 34a of the chamber 10 through interface 50 and to the dryness sensor 34b of boiler 20 through interface 56. Output signals from the microcontroller are directed to interfaces 58, 60 and 62 to control the operation of dosing pump 26, heating elements 20a of boiler 20, and valve V, respectively, to carry out the stages in a cycle of steam sterilization. Selected program parameters, such as the operating sterilization temperature, are entered by keyboard terminal 61. Information as to the status of the running sterilization program, such as the time remaining on a clock cycle, is displayed on terminal 63.

Figure 5:
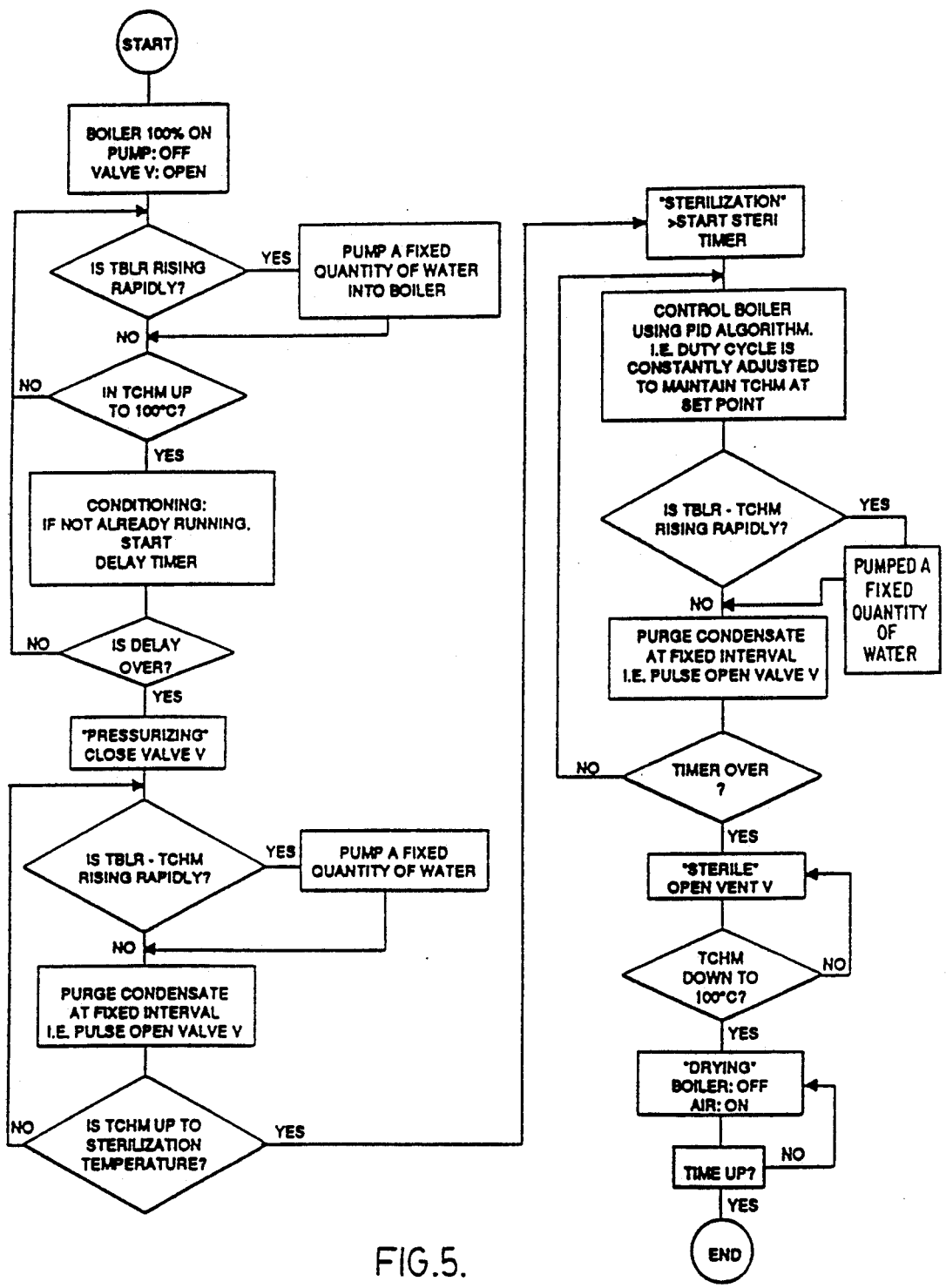
FIG. 5 is a flow-chart for electronic microprocessor control apparatus to control the operation of the system of FIG. 1, illustrating the steps of the process of the invention.

A flow-chart for the operation of the system of FIG. 1 under the control of such electronic sequencing means is given in FIG. 5. The operation identified as "Purge Condensate at Fixed Interval" relates to the step of opening valve V when the chamber is being pressurized, or during the sterilization period, at suitable intervals to vent condensate from the chamber and to close valve V when the release of gaseous steam from the chamber immediately upon expulsion of the condensate is sensed by a drop in the chamber temperature. By this expedient, the build-up of condensed water is precluded.

Figure 6:
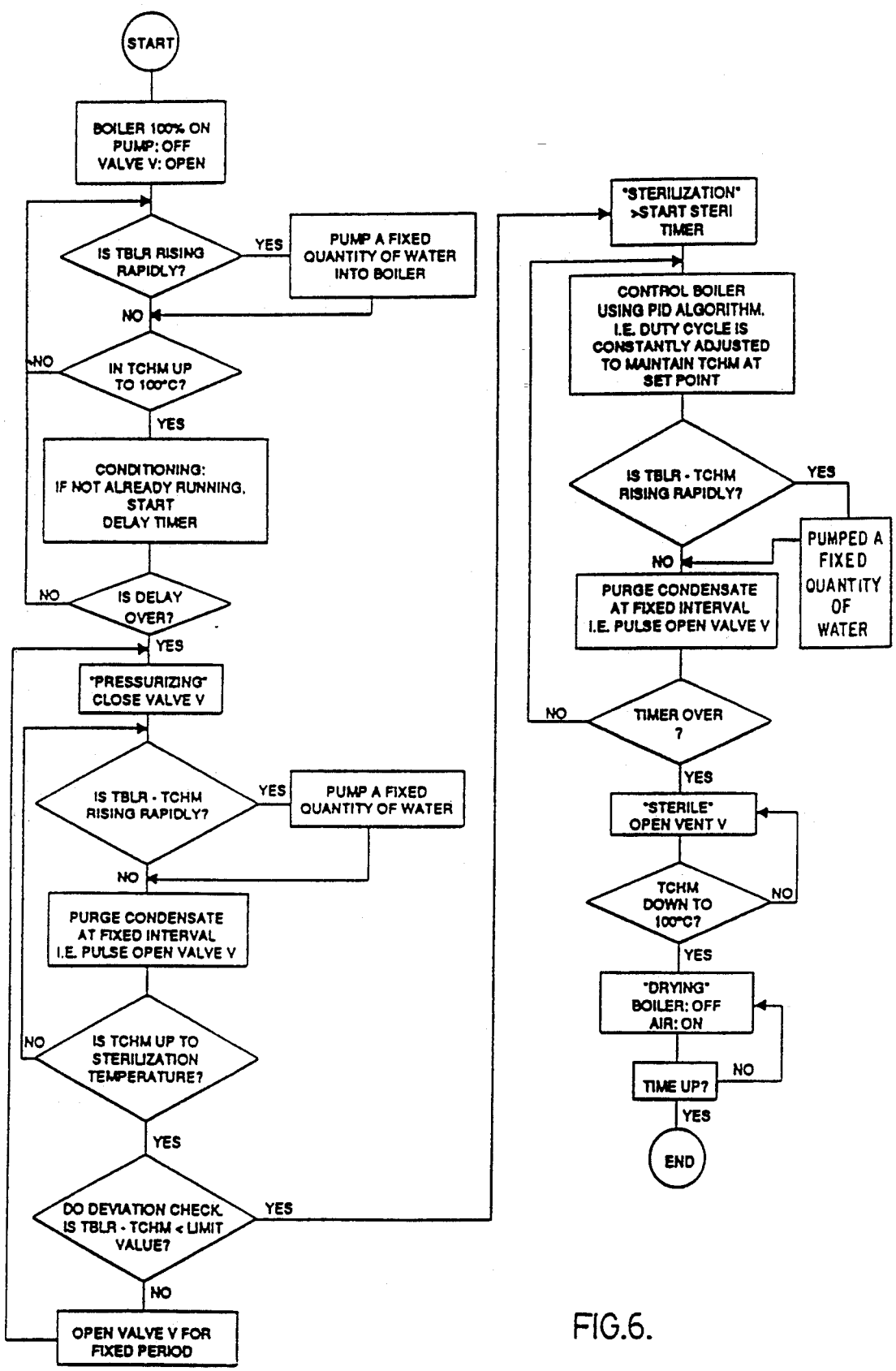
FIG. 6 is a further flow-chart for electronic microprocessor control apparatus, including the additional function of a deviation check, illustrating a further embodiment of the process of the invention.

FIG. 6 is a similar flow-chart to that of FIG. 5, but represents a control process which includes a further sequence loop involving the decision "Do Deviation Check". This is an additional safety feature which addresses the possibility that not all of the air has been purged from the chamber during the conditioning phase, as follows:

The small interior volume of the boiler and the continued boiling of water therein ensures that all air has been purged from the boiler itself shortly after the commencement of boiling, so that TBLR thereafter measures the steam table value of steam in the boiler, i.e. the boiling temperature of water in the absence of air at the given pressure. If substantially all of the air in the chamber has been purged during the purging and conditioning phases of the process, then TCHM will not depart markedly from TBLR, as illustrated in FIG. 3. If, however, any undesired air should remain in the chamber during sterilization, this will be reflected in a difference between the equilibrium temperature within the boiler and within the chamber, TBLR > TCHM, since the total pressure in the chamber is the sum of the partial pressures of air and saturated steam.

Accordingly, by the deviation check of the modified process diagrammed in FIG. 6, a comparison is made between TCHM and TBLR, taking a running average of both temperatures and ignoring the short-duration "peaks" in TBLR when the boiler runs dry. A value of this difference greater than a predetermined value indicates that there is excess air as well as saturated steam in the system. Vent valve V is then opened for a short fixed period of time to purge the unwanted air from the chamber, and sterilization is recommenced. The deviation check thus permits the control system to monitor and, if necessary, automatically ensure sterilization conditions in the chamber, without having to measure pressure directly anywhere in the system, by contrast with the standard autoclave chambers referred in the earlier discussion of prior art.

As discussed briefly in connection with FIG. 1 and the associated description of the system of the invention, there is provided according to the invention a novel sterilization chamber in the form of a cassette that can be plugged into a holder for coupling the chamber to the steam inlet and venting conduits of the system. In its broadest aspects the components and function of the novel cassette arrangement are illustrated schematically in FIG. 7 to 11.

As best seen in the exploded view of FIG. 7, and the assembled cassette in FIG. 8, the cassette sterilizing chamber 10 includes a bottom tray 10b preferably including a grid or perforated rack 12 resting in and spaced above the floor of the bottom of tray 10b for receiving dental instruments 17 or the like and enhancing their exposure to sterilizing steam in the chamber. The cassette 10 further includes a lid 10 a and a compressible sealing member 15 between lid 10a and 10b. The lid, bottom tray and rack should be constructed of a material exhibiting strength and resistance to attack by steam, such as stainless steel or anodized aluminum.

As best seen in FIG. 7 and in FIGS. 9 and 10, the latter two showing respectively partial and complete insertion of cassette 10 within holder 11, chamber 10 is provided with lower steam inlet and outlet ports 13 and 14, respectively. Steam injection conduit 18 and outlet conduit 16 plug sealingly into inlet and outlet ports 13 and 14, respectively when cassette 10 is fully inserted into holder 11, by O-rings or other conventional sealing members (not shown).

Rigid holder 11, which may be made of stainless or structural steel, has an inner insulating covering 11a to minimize loss of heat from cassette sterilization chamber 10 during operation. The small clearance between the top of lid 10a and the bottom of tray 10b and, respectively, the upper and lower inner surfaces of the insulating lining of holder 11 is chosen so that compressible sealing member 15 maintains its seal within holder 11 when chamber 10 is pressurized, but permits cassette chamber 10 to be withdrawn freely after sterilization when the chamber is vented or evacuated. Lid 10a is then removed, leaving the sterilized instruments in tray 10b for easy transportation, as illustrated in FIG. 11.

In the cassette illustrated in FIGS. 7 to 11, there is also shown the temperature sensor 34a required for monitoring the chamber temperature during sterilization when cassette 10 is used in the sterilization system of FIG. 1, and an aperture 35 in holder 11 for receiving the temperature sensor when the cassette 10 is inserted therein. When cassette 10 is used in steam sterilization, as for example in the controlled injection system of FIG. 1, sterilizing steam enters through conduit 18 into the rear of chamber 10. The flow of air and of condensed water toward outlet port 14 is directed by gravity through the expedient of mounting holder 11 at orthogonal angles $\alpha$ and $\beta$ out of the horizontal plane to make the corner of chamber 10 at outlet port 14 the lowest point.

A cassette sterilization chamber and holder as described above presents a number of advantages over the conventional autoclave typically used in the sterilization of instruments in dental or medical offices. Being in the form of a light weight, thin-walled tray inserted into an insulating jacket, the cassette chamber heats up quickly and uses less power in a sterilization cycle than a closed system autoclave. Pressurization of the cassette chamber can be carried out only when the cassette is fully inserted into the fixed rigid holder, eliminating the need for elaborate safety locking mechanisms as are required in autoclaves provided with doors. By its construction and manner of use, the cassette and holder arrangement of the present invention provide for sterilization of the very tray in which the instruments are cooled down for immediate use. No transfer from the interior of a sterilization chamber to an auxiliary carrying tray or other post-sterilization handling, of the kind necessary with conventional autoclaves, is involved.

In order to obtain effective purging of air from the chamber, it is desirable that the chamber be designed so as to minimize turbulent mixing of air initially present in the chamber with the sterilizing steam introduced into the chamber. A preferred embodiment of cassette sterilization chamber which is conducive to much better expulsion of air than a conventionally shaped autoclave and is of particular use in obtaining effective purging of air when used in conjunction with the system of FIG. 1 is illustrated in FIGS. 12 to 18. Structural components of this preferred embodiment of cassette sterilizer which are analogous to those of the cassette sterilizer of FIG. 7 to 11 are given the same reference numeral, but primed. Thus lid "10a" in FIG. 7 to 11 corresponds to lid "10'a" in FIGS. 12 to 18.

Figure 13:
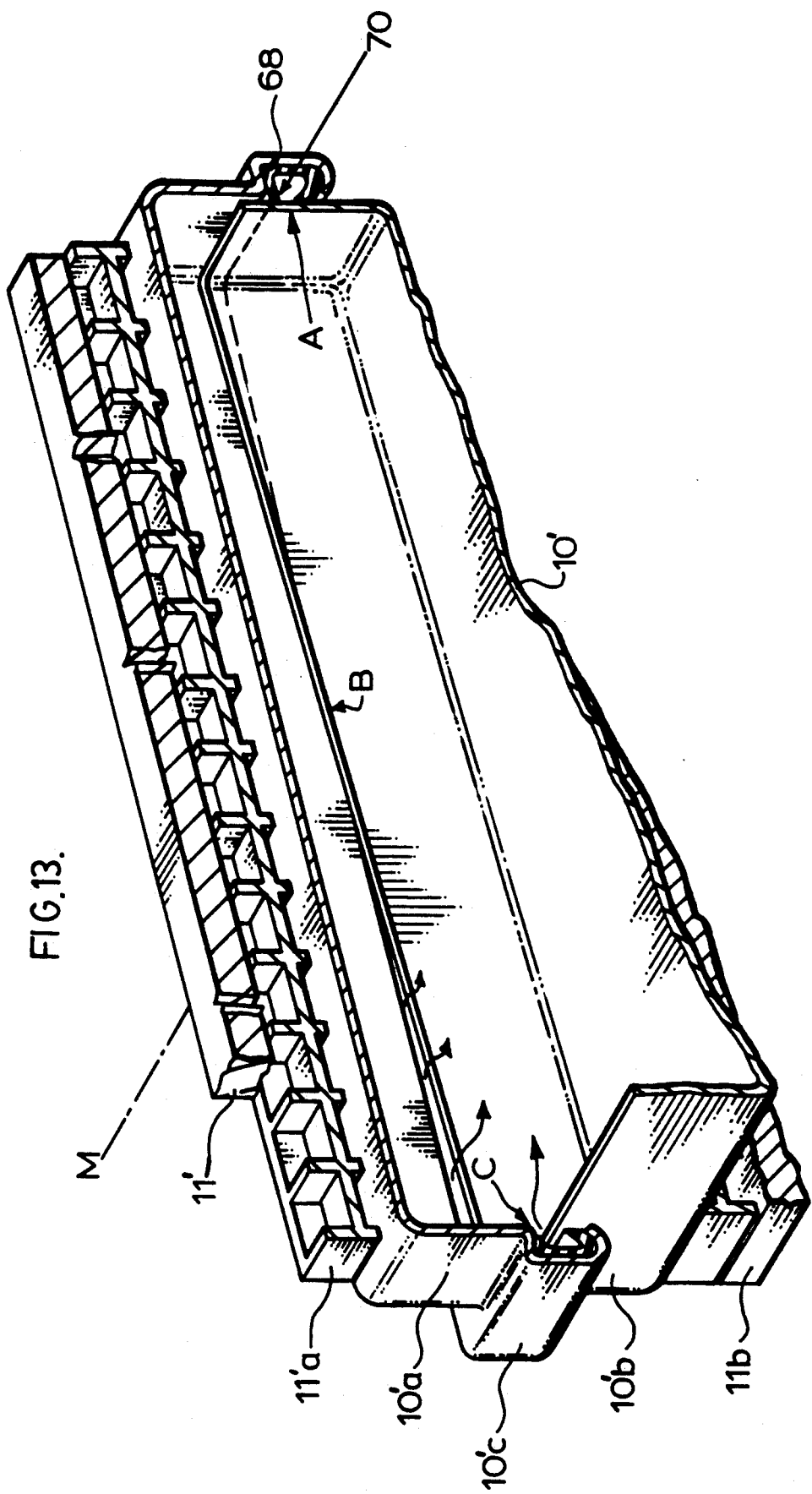
FIG. 13 is a sectional view, in perspective, taken along the line 13—13 in FIG. 12.
Figure 14:
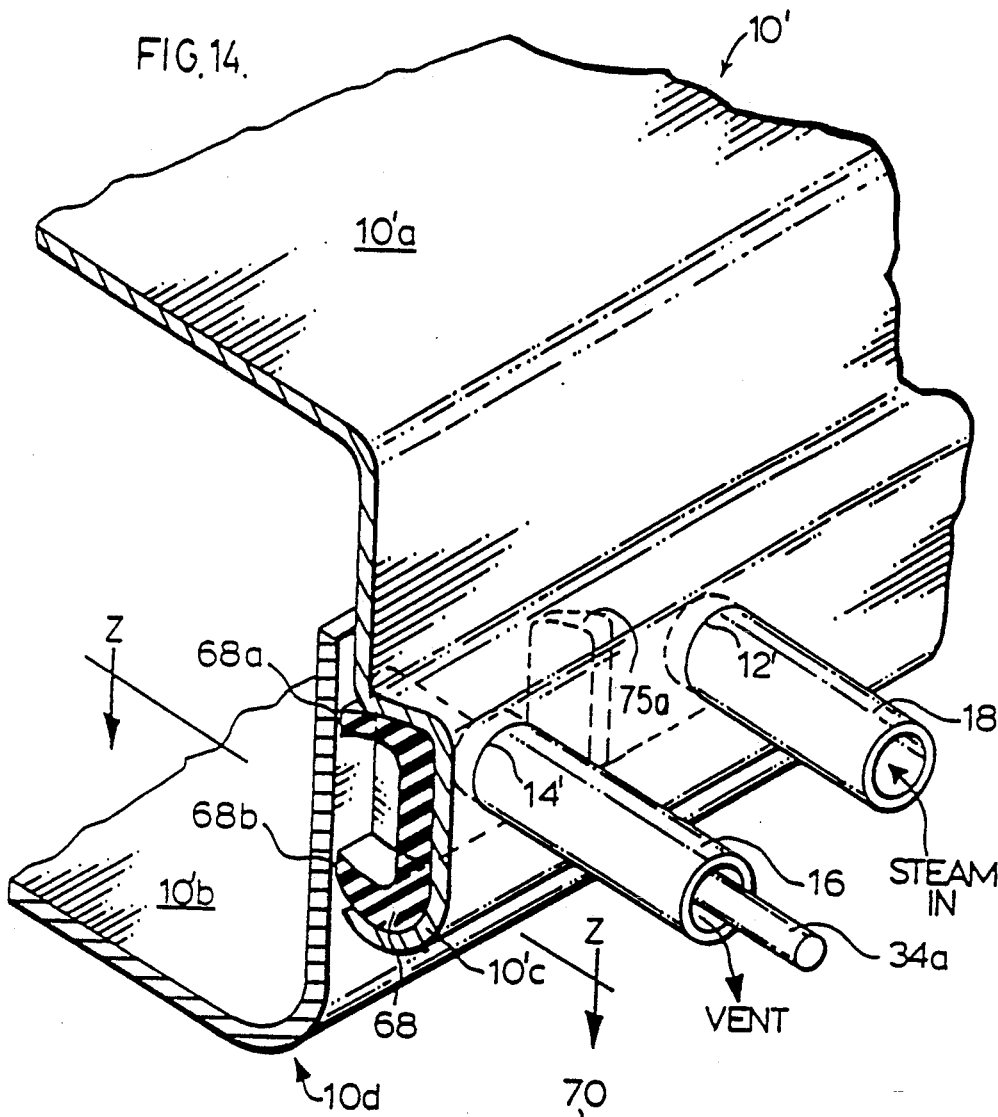
FIG. 14 is a detailed partial view in perspective of the arrangement of conduits and seals in the pressure chamber of FIG. 12, viewed generally along direction X.

As best seen in FIGS. 13 and 14, the chamber 10' comprises a lid 10'a and a bottom tray 10'b which holds dental or surgical instruments or other articles to be sterilized. Preferably, the instruments may be placed on or in a permeable holder (not shown) as in the cassette of FIG. 7 to 11. Again, the lid, bottom tray and rack should be constructed of a material exhibiting strength and resistance to attack by steam, such as stainless steel or anodized aluminum.

Fitted within an outwardly stepped perimetral channel 10'c at the base of lid 10'a is a flexible, unitary seal 68 having a generally J-shaped cross-section. As best seen in FIG. 14, when lid 10'a is installed over bottom tray 10'b in operation, the extremities of the J-seal contour abut against the outer wall of tray 10'b, as at points 68a and 68b, to form an interior channel 70 along the length of seal 68 closed off from the outside of chamber 10'. The shape and flexibility of seal 68 are such that pressurization of channel 70 by steam actuates the sealing action by flexing the lower wall of the seal more firmly against the tray. The principle of such self-actuating or self-energizing seals is well known and employed, for example, in pressure cookers and the lip seals used in hydraulic cylinders.

Lid 10'a is slightly wider and longer than bottom tray 10'b, but is prevented from slipping below its operating position by matching exterior stops on the lid and tray (not shown). Lid 10'a includes at one lower corner thereof ports 12' and 14' to receive and hold a steam injection conduit 18' and a venting conduit 16', respectively. In operation, a thermocouple 34a is inserted in venting conduit 16'.

Figure 15:
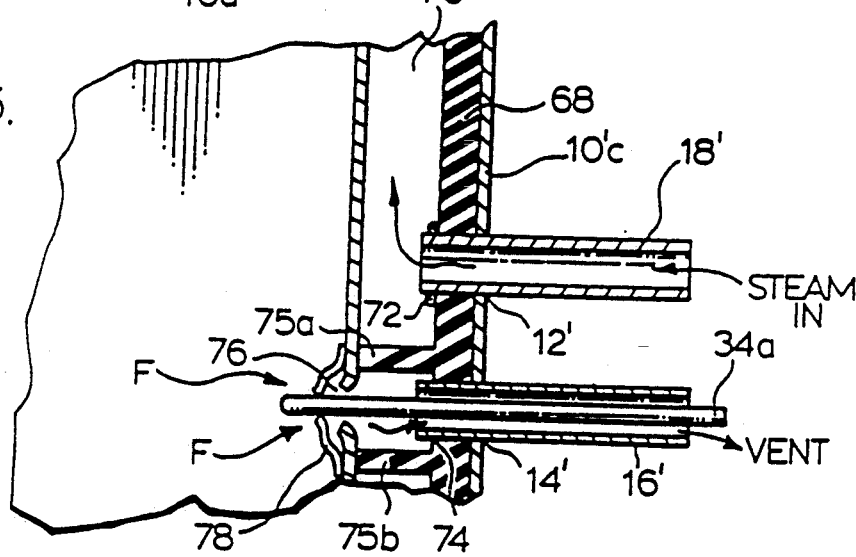
FIG. 15 is a detailed plan sectional view of the inlet and outlet area in the pressure chamber of FIG. 12.

In the preferred embodiment of cassette chamber of the invention, as best seen in FIG. 15, the self-actuating seal includes an inlet aperture 72 that is aligned with chamber wall inlet port 12 when lid 10'a is in place over tray 10'b, to receive the steam inlet conduit 18'. Steam injected into the chamber proceeds along channel 70 in the direction of the successive positions A, B and C indicated in FIGS. 12 and 13.

The seal 68 is formed with an outlet aperture 74 that aligns with lid wall outlet port 14, to receive the outlet (venting) conduit 16'. However, disposed to the sides of the outlet aperture 74 are a pair of integral partitions 75a and 75b, which close aperture 74 off from seal channel 70.

Figure 16:
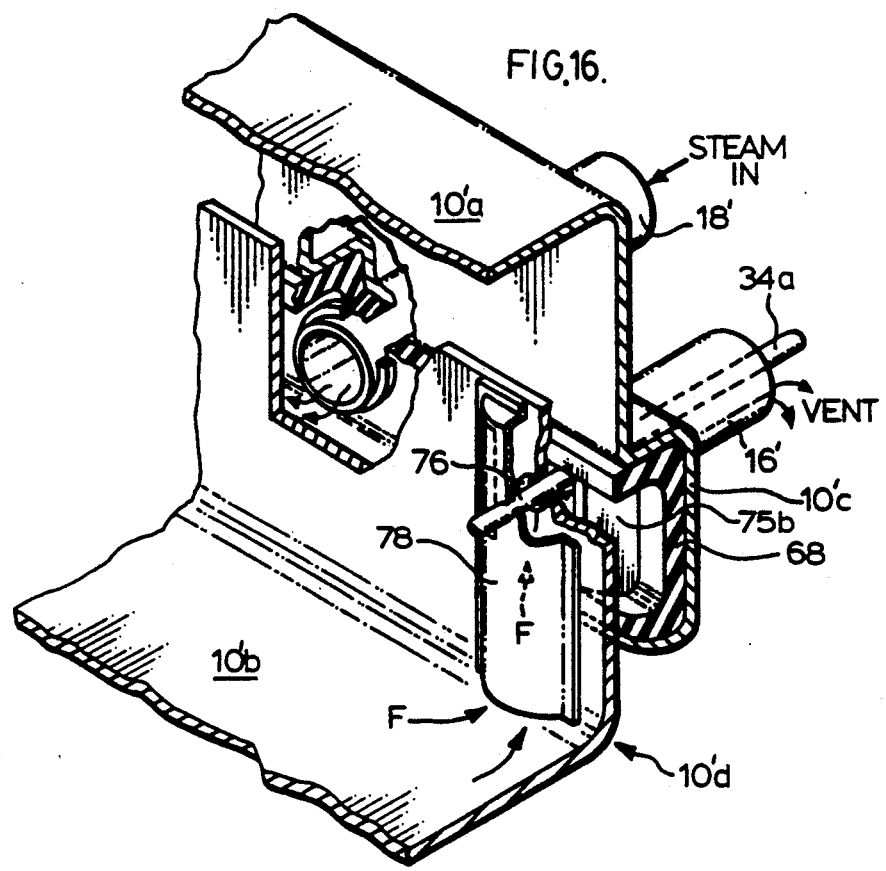
FIG. 16 is a three-dimensional detailed sectional view generally taken along the line 16—16 in FIG. 12.

As best seen in FIGS. 15 and 16, the interior of chamber 10' communicates with the vent conduit 16' through a tray wall aperture 76 aligned with lid wall outlet port 14' and seal outlet aperture 74. The effluent stream of gases and/or condensate purged from the interior of chamber 10, exits the chamber from the region of the bottommost corner 10'd, through a vertical channel member 78 open at the bottom near the floor of tray 10'b. The outflow of steam and condensate through channel member 78 is indicated by arrows F in FIGS. 15 and 16. Temperature sensor 34a may extend a short distance into the interior of chamber 10, through a peripherally sealed aperture in channel member 78, to hold it in place within the effluent stream.

Figure 12:
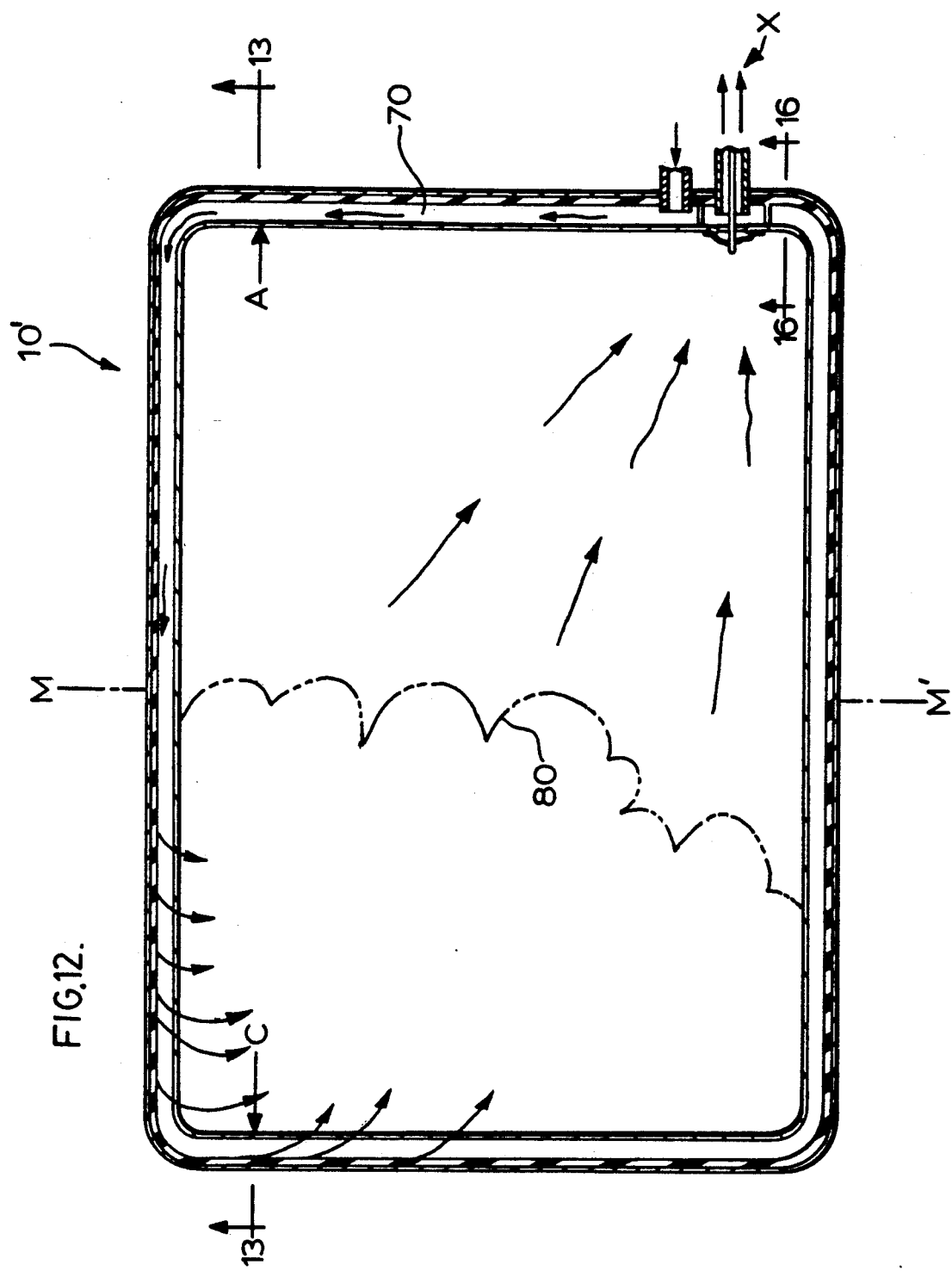
FIG. 12 is a sectional plan view of a preferred embodiment of cassette sterilization chamber according to the invention.

As best seen in FIGS. 12 and 13, the plane of the lid channel 10'c that holds seal 78 is tilted downwardly with respect to the upper edge of the bottom tray 10b about the transverse axis MM', so that when lid 10'a is set in place on tray 10'b, channel 70 is entirely occluded by the vertical side walls of tray 10b to that side of axis MM, disposed toward the steam inlet and outlet conduits, but communicates with the interior of the chamber to an increasing degree proceeding to the other side of axis MM'.

Thus, at position A along the channel, the seal 68 is entirely below the upper edge of tray 10'b. At position B, the upper contact of seal 68 with the tray just meets the upper edge of the tray, and by position C is displaced above that upper edge, so that steam initially introduced within channel 70 vents into the interior of the chamber.

The result of this arrangement of seal and chamber components is that steam injected into the seal channel 70 at one corner of the chamber 10 enters the tray along the opposite corner of the chamber and proceeds across the chamber toward the vent. A high-velocity flow of steam from the boiler is thereby converted to a low-velocity piston-like front of steam 80, which efficiently and without turbulence pushes chamber atmosphere out ahead of it.

Figure 17:
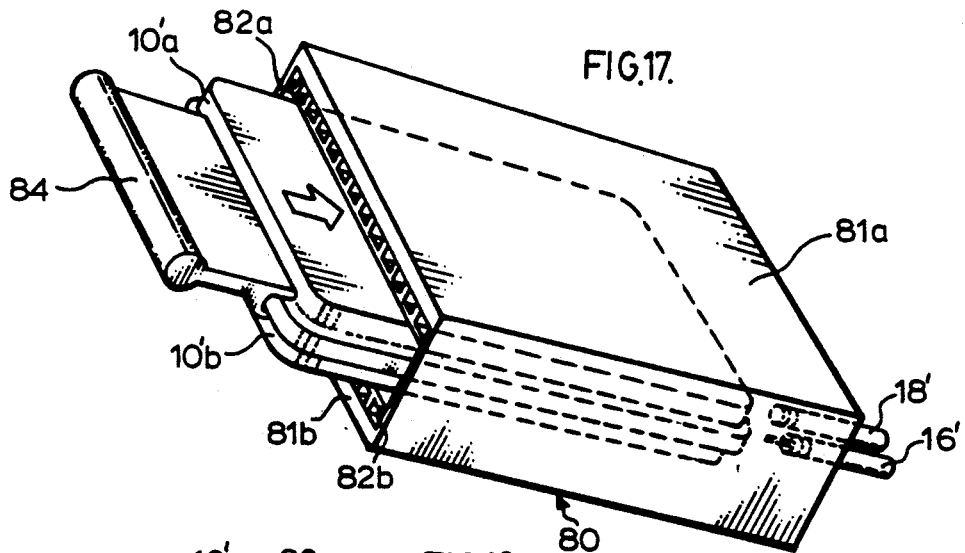
FIG. 17 illustrates the installation of the pressure chamber of FIG. 12 into insulated holding means for connection to steam inlet and venting conduits in the system of the invention.
Figure 18:
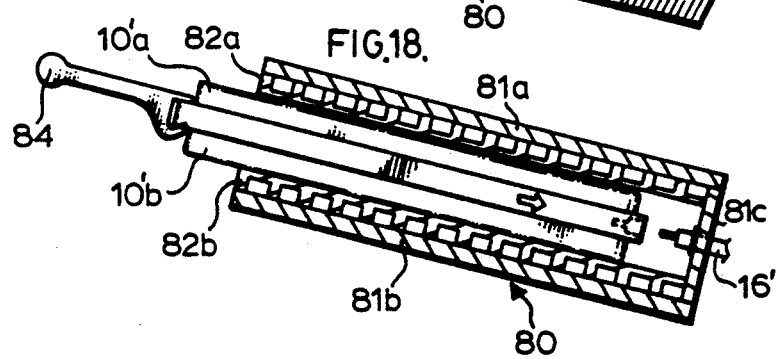
FIG. 18 is a further view in vertical section of the pressure chamber and holding means of FIG. 17.

FIGS. 17 and 18 illustrate the holding means for use in association with the pressure chamber of FIGS. 12-18. Indicated generally at 80, the holder comprises a pair of retaining plates 81a and 81b having respective insulated coverings 82a and 82b with textured surfaces, such as small rectangular bosses. This arrangement minimizes loss of heat from chamber 10' during operation. Too, the spacing between seal as described above and the upper and lower holding plates is chosen that the chamber is held tight between the plates when pressurized but can be manually inserted freely before commencement of sterilization and removed freely after sterilization by means of a gripping handle 84 when the chamber is vented or evacuated. When the interior channel 70 of self-actuating seal 68 is pressurized, the extending arms of the seal bulge slightly away from each other to exert oppositely directed forces on lid 10'a and tray 10'b, forcing them against insulating plates 82a and 82b.

As illustrated in FIGS. 17 and 18, holder 80 may be assembled as a modular unit in which the chamber can be slid between the holding plates and plugged into a socket in an integral rear wall 81c of the unit, holding the inlet conduit 18 and outlet conduit 16 connected to the rest of the sterilization apparatus, such as that illustrated in FIG. 1. It has been found with a system constructed with the sterilization system of the invention and the preferred embodiment of cassette chamber that the sterilization and drying of surgical or dental instruments can be efficiently completed within a few minutes.

It will be understood that various forms of injector pumps or valves may be employed in the system of the invention. Electrically controlled valves, temperature sensors and eductor pumps, as well as equivalent devices, are readily available commercially and their manner of operation well known in the art. It is the combination of elements and their manner of control which the present teaching provides which provides the unique aspects of the invention. Accordingly, reference should be made to the appended claims in evaluating the scope thereof.

I claim:

1. A system of steam sterilizing articles, comprising:
   (a) a pressure chamber for holding the articles to be sterilized, having an inlet conduit for steam and an outlet conduit;
   (b) means for venting the interior of said chamber, comprising a first valve in said outlet conduit having an open position and a closed position, and valve control means for switching the first valve between its open and closed positions;
   (c) means for injecting steam into said chamber, comprising:
      (i) an electrically heated boiler in communication with said pressure chamber through said steam inlet conduit, and boiler control means for the electrical power supplied to said boiler, and
      (ii) pump means for injecting a pulse of water of a predetermined quantity from a water container into said boiler to produce steam, and pump control means to actuate said pump means
   (d) first temperature sensor means for monitoring the temperature at said outlet conduit when venting the pressure chamber and the temperature of steam in said chamber when pressurized by steam,
   (e) a boiler dryness sensor means with said boiler with a second temperature sensor means for detecting an abrupt increase in temperature as a function of time which is indicative of vaporization of all of the liquid in said boiler; and
   (f) sequencing means responsive to said, first temperature sensor means and to said sensor boiler dryness means for controlling the operation of said valve control means, said boiler control means and said pump control means, said sequencing means being configured to perform the following steps:
      (i) actuating said pump control means only when the boiler is dry, to cause a pulse of water to be injected into the boiler, (ii) in an initial air purging phase, actuating said valve control means to close said first valve means a predetermined period of time following attainment of a predetermined chamber outlet threshold temperature indicating the venting of saturated steam from the chamber, (iii) when a predetermined desired sterilization temperature has been attained in the pressurized chamber, actuating said boiler control means to modulate the electrical power supplied to the boiler, so as to maintain said sterilization temperature substantially constant within the chamber over a selected sterilization period, and (iv) upon completion of sterilization at the end of said sterilization period, actuating said valve control means to open said first valve means to depressurize the chamber and actuating said boiler control means to turn the boiler off.

2. A system according to claim 1, wherein said first and second temperature sensor means each comprises a thermocouple.

3. A system according to claim 1, wherein said sequencing means is configured to perform the further step of actuating said valve control means to open said first valve means at suitable intervals when the chamber is being pressurized and during sterilization to vent condensate from the chamber, and to close said first valve means when expulsion of the condensate is detected by an abrupt drop in the chamber outlet temperature.

4. A system according to claim 1, further comprising:
(a) a source of clean, dry compressed air connected by a branch conduit to said pressure chamber steam inlet conduit;
(b) means in said branch conduit for controlling the flow of compressed air into said chamber inlet conduit, so that said source may be closed off from the system during sterilization and a stream of drying air may be passed through said chamber following completion of a sterilizing cycle.

5. A system according to claim 1, wherein said second temperature sensor means is also operable to monitor the temperature of the steam in the boiler.

6. A system according to claim 5 wherein said sequencing means is configured to perform the additional step, when a predetermined desired sterilization temperature has been attained in the pressurized chamber, of comparing the sensed temperature from the first temperature sensor to the sensed temperature from the second temperature sensor. and, if the difference between the two temperatures exceeds a predetermined limit indicative of the presence of residual unpurged air in the chamber, opening said vent valve for a brief period to permit purging of said residual air and then closing the vent valve.

7. Apparatus for producing a vapor from a liquid comprising:
boiler means for vaporizing said liquid,
pump means for supplying discrete doses of said liquid to said boiler means,
control means for detecting when substantially all of said liquid supplied to said boiler means has been vaporized comprising a temperature sensing means fixed within the boiler for detecting an abrupt increase in temperature as a function of time and means for causing said pump means to supply a said dose of said liquid to said boiler means in response to the abrupt increase in temperature as a function of time from the temperature sensing means whereby heating power available to said boiler is maximally employed in the production of said vapor.

8. Apparatus according to claim 7 wherein said means for determining the temperature of said boiler comprises a thermocouple in contact with a boiling chamber of said boiler.

9. Apparatus according to claim 8 wherein said thermocouple is also in contact with any liquid remaining in said boiling chamber.

10. Apparatus according to claim 9 wherein said liquid is water.